United States Patent
Baratella et al.

(10) Patent No.: US 9,428,468 B2
(45) Date of Patent: Aug. 30, 2016

(54) PROCESS FOR THE PREPARATION OF ERLOTINIB

(71) Applicant: CERBIOS-PHARMA SA, Barbengo/Lugano (CH)

(72) Inventors: Marco Baratella, Cerano (IT); Giuseppe Pallanza, Robbio (IT); Mauro Gaboardi, Novara (IT); Graziano Castaldi, Briona (IT)

(73) Assignee: CERBIOS-PHARMA SA, Barbengo/Lugano (CH)

( * ) Notice: Subject to any disclaimer, the term of this patent is extended or adjusted under 35 U.S.C. 154(b) by 0 days.

(21) Appl. No.: 14/923,875

(22) Filed: Oct. 27, 2015

(65) Prior Publication Data

US 2016/0115137 A1 Apr. 28, 2016

(30) Foreign Application Priority Data

Oct. 28, 2014 (IT) ................ MI2014A1845

(51) Int. Cl.
*C07D 239/94* (2006.01)
*A61K 31/517* (2006.01)

(52) U.S. Cl.
CPC ........... *C07D 239/94* (2013.01); *A61K 31/517* (2013.01)

(58) Field of Classification Search
CPC ..................... A61K 31/517; C07D 239/94
See application file for complete search history.

(56) References Cited

U.S. PATENT DOCUMENTS 7,960,545 B2   6/2011   Jyothi Prasad et al.

FOREIGN PATENT DOCUMENTS

| EP | 1044969 | 10/2000 |
|---|---|---|
| EP | 2433934 | 3/2012 |
| IN | WO 2010/109443 | * 9/2010 |
| WO | 96/30347 | 10/1996 |
| WO | 2007138612 A2 | 12/2007 |
| WO | 2007138613 A2 | 12/2007 |
| WO | 2010109443 A1 | 9/2010 |

OTHER PUBLICATIONS

Chandregowda (Organic Chemistry: An Indian Journal (2009), 5, (4), 397-400.*
Chandregowda et al., "Convergent Approach for Commercial Synthesis of Gefitinib and Erlotinib", Organic Process Research & Development, 2007, vol. 11, pp. 813-816.
European search report based on IT MI20141845.

* cited by examiner

*Primary Examiner* — Valerie Rodriguez-Garcia
(74) *Attorney, Agent, or Firm* — Lucas & Mercanti, LLP

(57) ABSTRACT

A process for the preparation of Erlotinib is disclosed in which the compound of formula (II)

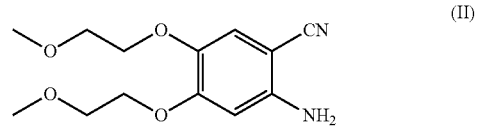

Is reacted with the compound of formula (III) in the presence of trifluoroacetic acid and formamidine acetate, in an aprotic solvent,

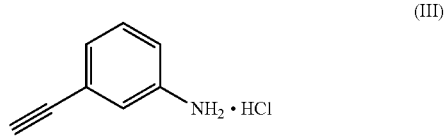

and the reaction product is subsequently treated with a source of hydrochloric acid in a suitable solvent to give Erlotinib hydrochloride.

10 Claims, No Drawings

PROCESS FOR THE PREPARATION OF ERLOTINIB

CROSS-REFERENCE TO RELATED APPLICATIONS

This application claims the benefit of priority from Italian Patent Application Serial No. MI2014A001845, filed Oct. 28, 2014, the contents of which are incorporated herein by reference.

FIELD OF THE INVENTION

The present invention relates to a process for the synthesis of Erlotinib and intermediates useful for its preparation.

BACKGROUND OF THE INVENTION

Erlotinib is a drug used in the treatment of cancer diseases, in particular for lung and pancreatic cancer. Erlotinib is an inhibitor of the tyrosine kinase receptor, acting in particular by inhibiting the EGF receptor, the epidermal growth factor receptor; in cancer there is the over-expression of growth factor receptors and related ligands. These are, in fact, some of the factors involved in processes of cancer etiopathogenesis. The stimulation of the growth factors leads to an increase of the cell proliferation with the consequent starting of the disease. The receptors, once bound the ligand, self-phosphorylate so generating a cascade of intracellular reactions that lead to the activation of transcription factors involved in the cell proliferation. Erlotinib binds itself to the intracellular catalytic portion of the receptor miming the ATP structure, but being more stable than that, they bind to the receptor and inhibit it. Therefore the activation of the cell reactions is not allowed, so blocking the cell expansion.

Erlotinib is a compound of formula (I)

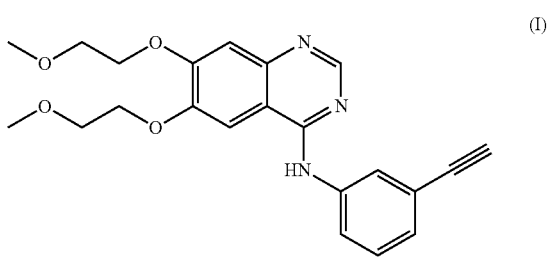 [SMILES: C#Cc1cccc(Nc2ncnc3cc(OCCOC)c(OCCOC)cc23)c1]

chemically known as N-3-(ethynyl-phenyl)-6,7-bis-(2-methoxyethoxy)-4-quinazolin amine, described in WO 96/30347 and marketed with the trademark Tarceva®.

WO 96/30347 describes a process for the synthesis of Erlotinib reported in the following scheme 1:

Scheme 1

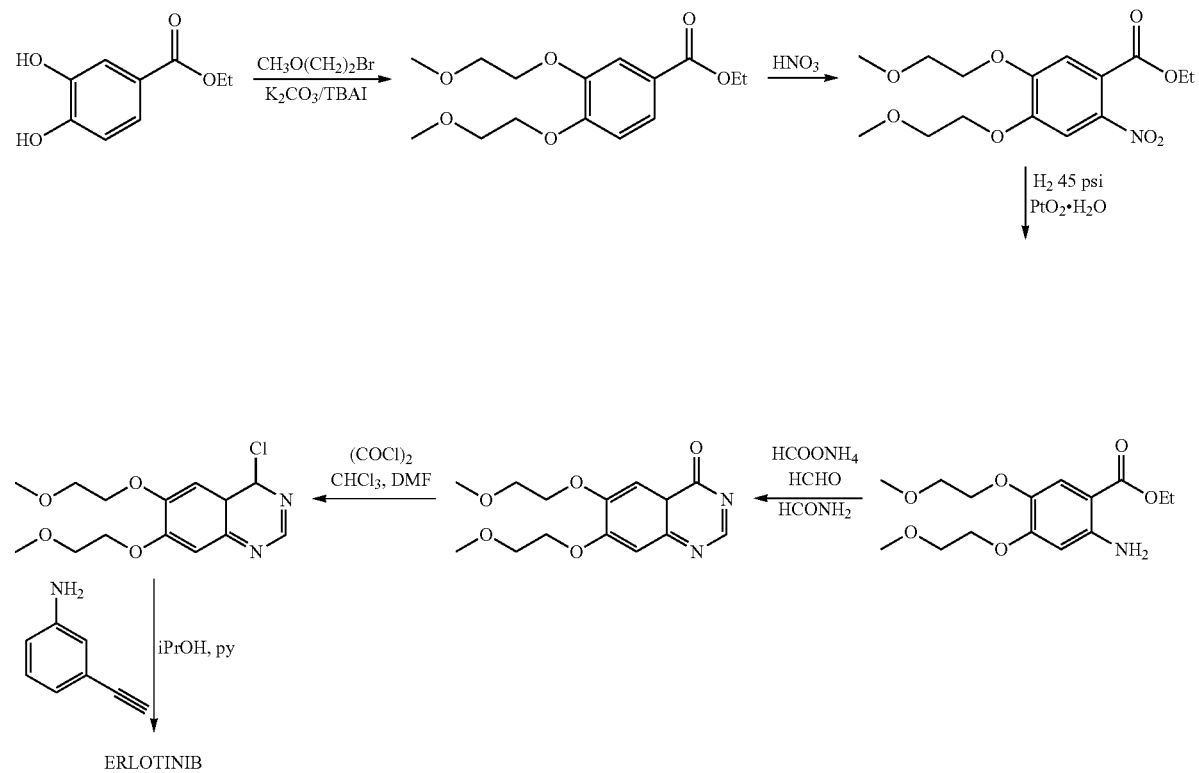

ERLOTINIB

EP 1 044 969 describes a process for the synthesis of Erlotinib reported in the following scheme 2:

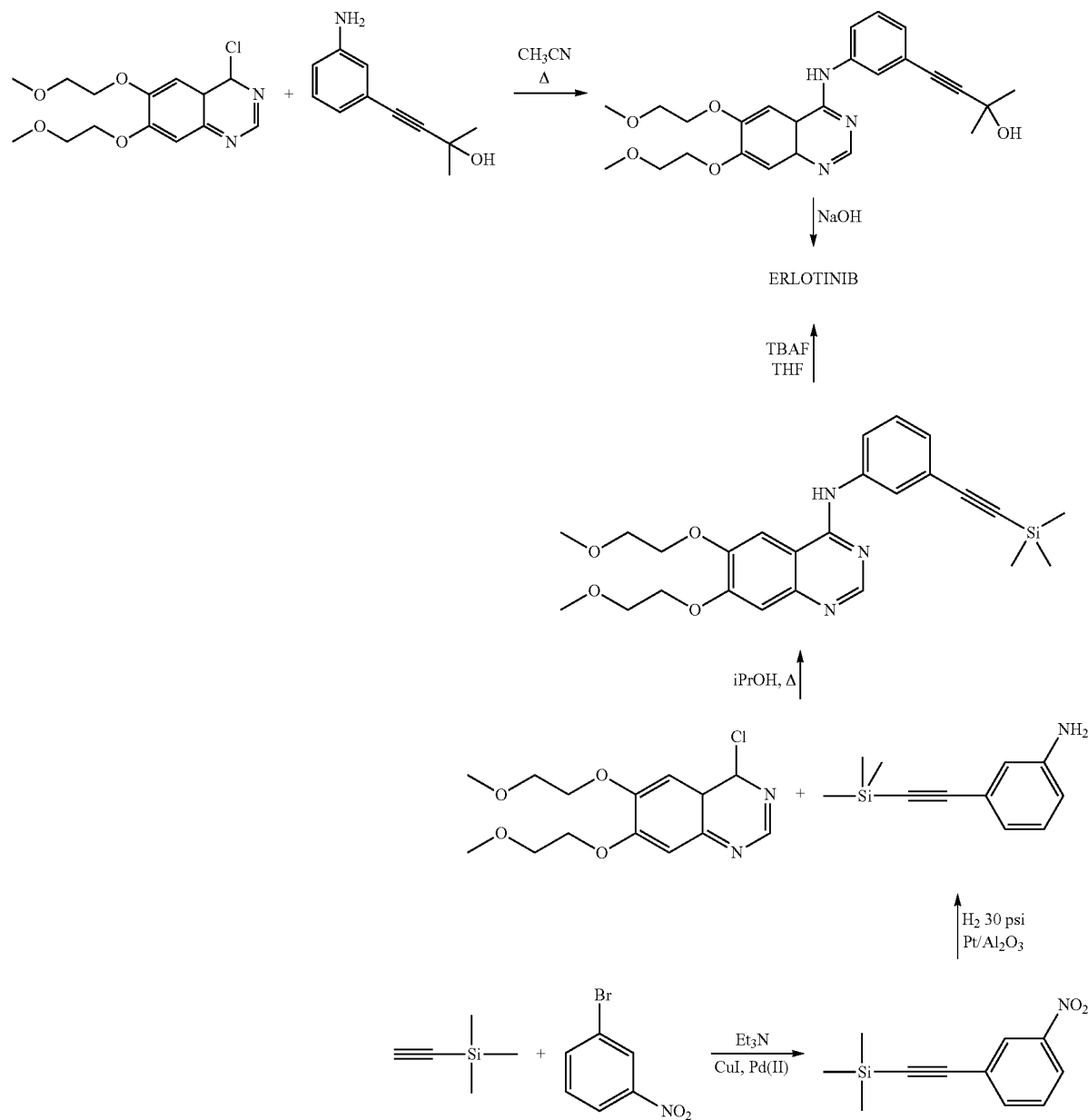
U.S. Pat. No. 7,960,545 discloses a process for the synthesis of Erlotinib reported in the following scheme 3:
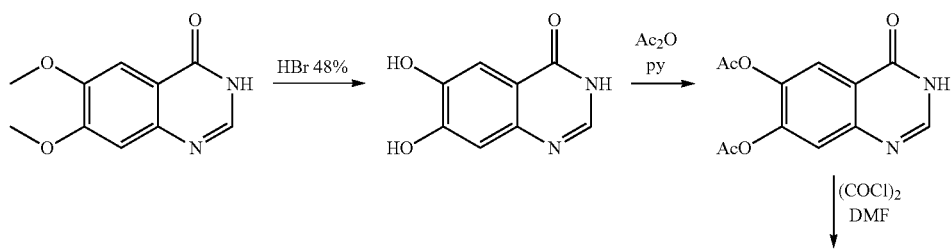

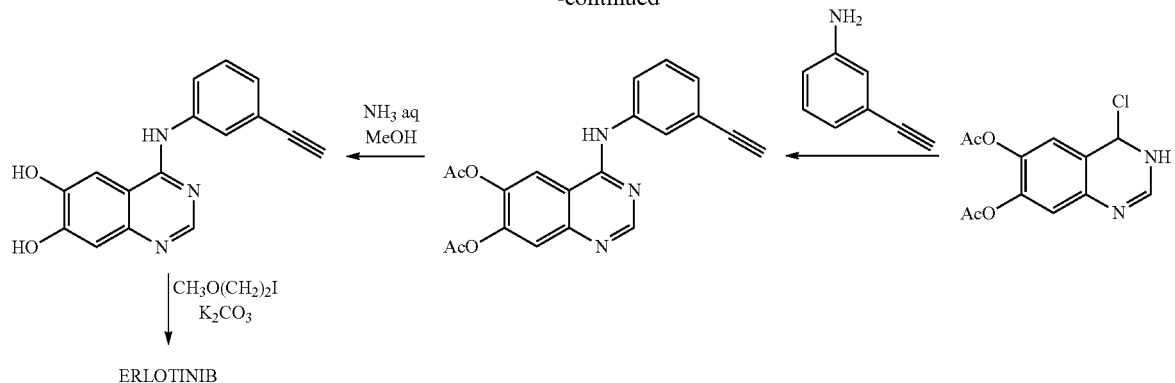
EP 2 433 934 describes a process for the synthesis of Erlotinib reported in the following scheme 4:
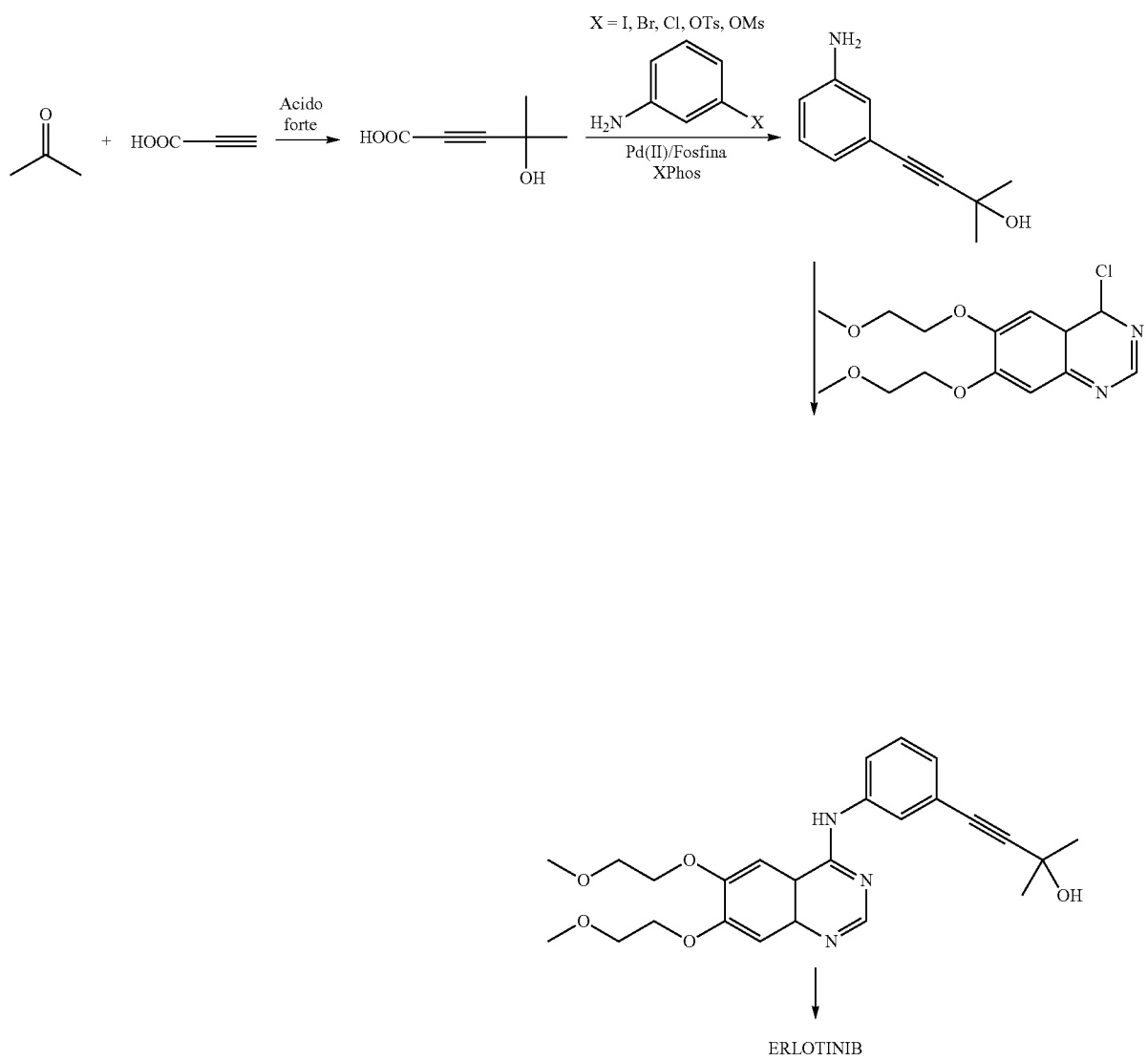

All these processes foresee numerous steps for the preparation of the key intermediate, 4-chloro-6,7-bis(2-methoxyethoxy)quinazoline, that is then reacted with 3-ethynylaniline or a derivative thereof.

WO 2007/138612 and WO 2007/138613 describe a process for the synthesis of Erlotinib reported in the following scheme 5:

necessarily require the formation and the isolation of the intermediate obtained by the reaction with N,N-dimethylformamide dimethylacetal.

We have now found that it is possible to further reduce the number of synthetic steps, the use of expensive reagents and the isolation of intermediates so obtaining Erlotinib through a simpler and cheaper process.

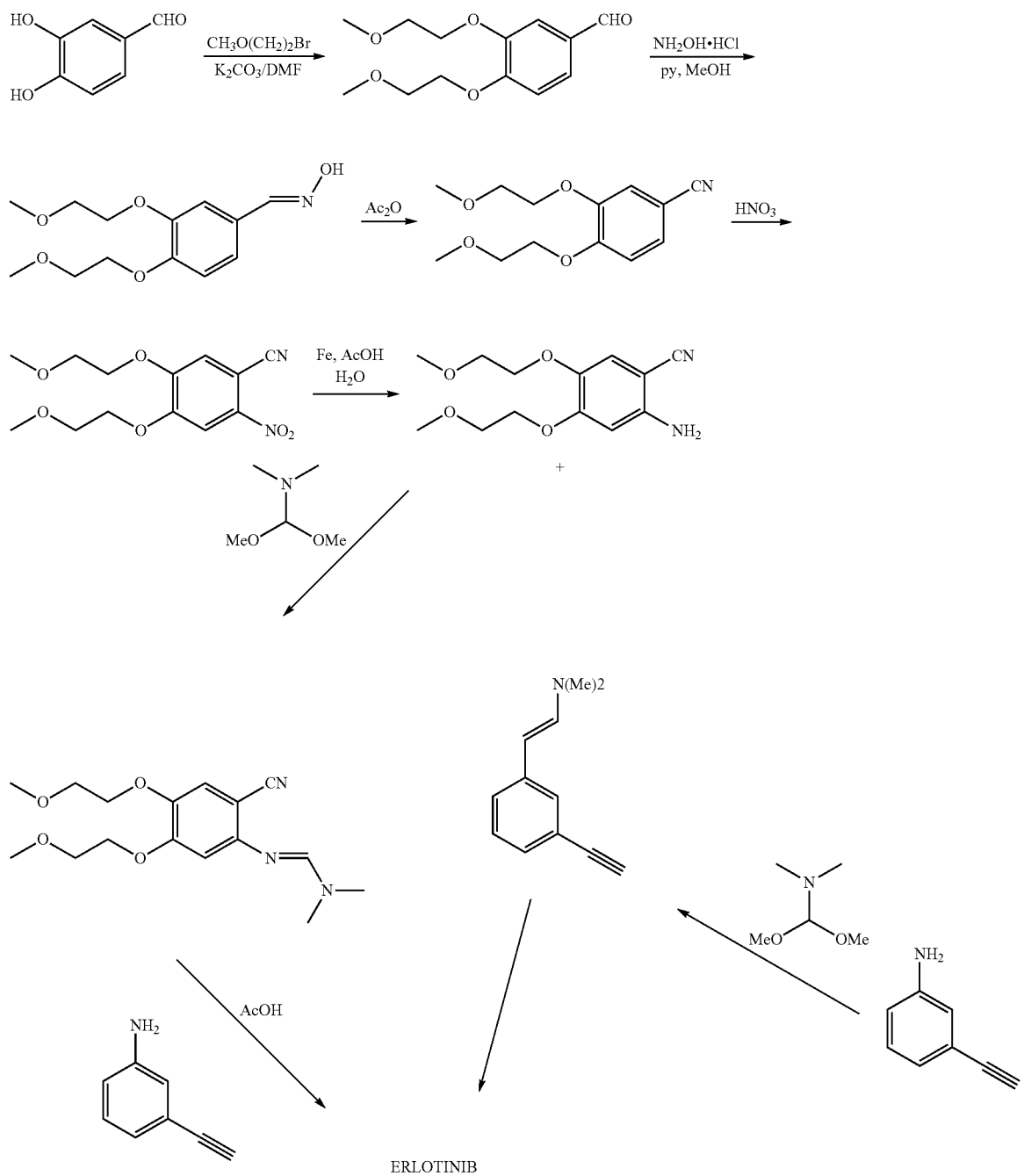

The processes described in WO 07/138612 and WO 07/138613 have the advantage to reduce the number of steps avoiding the formation and the isolation of the intermediate 4-chloro-6,7-bis(2-methoxyethoxy)quinazoline but they

SUMMARY OF THE INVENTION

It is therefore object of the present invention a process for the synthesis of Erlotinib comprising:

a) the reaction of the compound of formula (II)

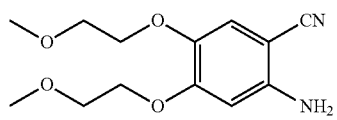

(II)

with the compound of formula (III)

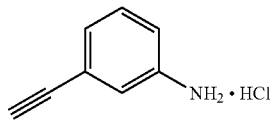

(III)

b) the subsequent treatment with a source of hydrochloric acid in a suitable solvent to give Erlotinib hydrochloride.

DETAILED DESCRIPTION OF THE INVENTION

The compounds (II) and (III) are both known and commercially available or prepared according to methods described in literature (for example in WO 2007/138612). The reaction between the compound of formula (II) and the compound of formula (III) of the process object of the present invention is preferably carried out in the presence of trifluoroacetic acid and formamidine acetate in an aprotic polar solvent selected among acetonitrile, isopropanol, N,N-dimethylformamide, N,N-dimethylacetamide and tetrahydrofuran, preferably acetonitrile.

The reaction between the compound (II) and the compound (III) represents the most characteristic feature of the process object of the present invention since it allows to carry out one-pot the formation of the quinazoline ring and its functionalization with the 3-ethynylphenylamino group without requiring the isolation of any intermediate and directly obtaining Erlotinib.

In particular, the use of formamidine acetate makes the process of the invention different from all the known methods, in particular also from the methods described in WO 07/138612 and in WO 07/138613, which foresee different intermediates and mechanisms of action.

In the subsequent step of the process object of the present invention a treatment with a source of hydrochloric acid is carried out to obtain Erlotinib hydrochloride.

Preferably, the source of hydrochloric acid can be a solution of hydrochloric acid or an amine hydrochloride salt, preferably selected among benzylamine hydrochloride, trymethylamine hydrochloride, triethylamine hydrochloride. An aqueous solution of concentrated hydrochloric acid is more preferably used.

The treatment with a source of hydrochloric acid is carried out in a suitable solvent preferably selected among isopropanol, methanol, butanol, ethyl acetate and tetrahydrofuran. Isopropanol and ethyl acetate are the most preferred solvents.

In a preferred embodiment of the process object of the present invention the reaction between the compounds of formula (II) and (III) is carried out in the presence of formamidine acetate and trifluoroacetic acid in acetonitrile at a warm temperature, above room temperature and, as shown in the examples, at the reflux temperature of the solvent, and the subsequent treatment with concentrated hydrochloric acid is carried out in ethyl acetate as solvent, at room or slightly lower temperature. Erlotinib hydrochloride is so obtained with high yield and high degree of purity.

Although the present invention has been described in its characterizing features, equivalents and modifications obvious to the skilled in the art are included in the present invention.

The present invention will be now illustrated through some examples without limiting the scope of the invention.

All the terms used in the present invention, unless otherwise indicated, are to be understood in their common meaning as known in the art. Other more specific definitions for certain terms, as used in the present description, are highlighted herein after and constantly applied in the whole description and claims, unless a different definition provides specifically a broader meaning.

Example 1

In a reaction flask, 2-amino-4,5-bis(2-methoxyethoxy)-benzonitrile (37.01 g, 0.139 mol) and acetonitrile (185 ml) were charged; 3-ethynylaniline hydrochloride (30.00 g, 0.195 mol), trifluoroacetic acid (17.43 g, 0.152 mol) and formamidine acetate (15.19 g, 0.145 mol) were added to the resultant mixture. The reaction mixture was brought to the reflux temperature of the solvent and maintained under such conditions for about fifteen hours. At the end of the reaction, the temperature was brought to about 25° C., the solvent was removed by distillation under vacuum and methylethylketone (430 ml) was added. The organic phase was washed with a saturated sodium bicarbonate solution (2×100 ml) and with water (2×100 ml). The collected organic phases were concentrated to residue by distillation under vacuum.

The resultant raw product was suspended in ethyl acetate (450 ml) and a solution of hydrochloric acid at 37% (14.38 g, 0.145 mol) was added, maintaining the temperature at 15° C. for about thirty minutes. The resultant solid was filtered, washed and dried in oven under vacuum at 45° C. to give 36.02 g of Erlotinib HCl.

Example 2

In a reaction flask, 2-amino-4,5-bis(2-methoxyethoxy)-benzonitrile (37.01 g, 0.139 mol) and acetonitrile (185 ml) were charged; 3-ethynylaniline hydrochloride (30.00 g, 0.195 mol), trifluoroacetic acid (17.43 g, 0.152 mol) and formamidine acetate (15.19 g, 0.145 mol) were added to the resultant mixture. The reaction mixture was brought to the reflux temperature of the solvent and maintained under such conditions for about fifteen hours. At the end of the reaction, the temperature was brought to about 25° C., the solvent was removed by distillation under vacuum and methylethylketone (430 ml) was added. The organic phase was washed with a saturated sodium bicarbonate solution (2×100 ml) and with water (2×100 ml). The collected organic phases were concentrated to residue by distillation under vacuum.

The resultant raw product was suspended in ethyl acetate (450 ml) and benzylamine hydrochloride (20.82 g, 0.145 mol) was added, maintaining the temperature at 15° C. for about thirty minutes. The resultant solid was filtered, washed and dried in oven under vacuum at 45° C. to give 34.31 g of Erlotinib HCl.

Example 3

In a reaction flask, 2-amino-4,5-bis(2-methoxyethoxy)-benzonitrile (37.01 g, 0.139 mol) and acetonitrile (185 ml)

were charged; 3-ethynylaniline hydrochloride (30.00 g, 0.195 mol), trifluoroacetic acid (17.43 g, 0.152 mol) and formamidine acetate (15.19 g, 0.145 mol) were added to the resultant mixture. The reaction mixture was brought to the reflux temperature of the solvent and maintained under such conditions for about fifteen hours. At the end of the reaction, the temperature was brought to about 25° C., the solvent was removed by distillation under vacuum and methylethylketone (430 ml) was added. The organic phase was washed with a saturated sodium bicarbonate solution (2×100 ml) and with water (2×100 ml). The collected organic phases were concentrated to residue by distillation under vacuum.

The resultant raw product was suspended in ethyl acetate (450 ml) and trimethylamine hydrochloride was added, maintaining the temperature at 15° C. for about thirty minutes. The resultant solid was filtered, washed and dried in oven under vacuum at 45° C. to give 35.01 g of Erlotinib HCl.

The invention claimed is:

1. A process for the synthesis of Erlotinib hydrochloride, comprising:

a) reacting the compound of formula (II)

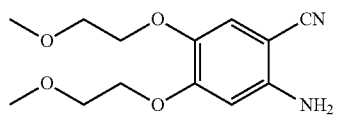

(II)

with the compound of formula (III)

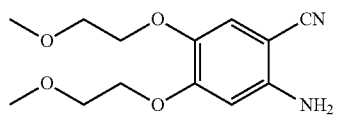

(III)

and b) subsequently treating the reaction product of step a) with a source of hydrochloric acid in a suitable solvent to give Erlotinib hydrochloride, wherein the reacting of the compound of formula (II) with the compound of formula (III) is carried out in the presence of trifluoroacetic acid and formamidine acetate, in an aprotic solvent.

2. The process of claim 1, wherein the aprotic polar solvent is selected from the group consisting of acetonitrile, isopropanol, N,N-dimethyl-formamide, N,N-dimethylacetamide and tetrahydrofuran.

3. The process of claim 2, wherein the solvent is acetonitrile.

4. The process of claim 1, wherein the source of hydrochloric acid is a solution of hydrochloric acid or an amine hydrochloride salt.

5. The process of claim 4, wherein the amine hydrochloride salt is selected from the group consisting of benzylamine hydrochloride, trimethylamine hydrochloride and triethylamine hydrochloride.

6. The process of claim 4, wherein the source of hydrochloric acid is an aqueous solution of concentrated hydrochloric acid.

7. The process of claim 1, wherein the treating with a source of hydrochloric acid is carried out in a solvent selected from the group consisting of isopropanol, methanol, butanol, ethyl acetate and tetrahydrofuran.

8. The process of claim 7, wherein the solvent is isopropanol or ethyl acetate.

9. The process of claim 1, wherein the reacting of the compounds of formula (II) and (III) is carried out in the presence of formamidine acetate and trifluoroacetic acid in acetonitrile at a temperature above room temperature and the subsequent treating with concentrated hydrochloric acid is carried out in ethyl acetate as solvent, at room temperature or slightly lower temperature.

10. The process of claim 1, wherein the reacting of the compounds of formula (II) and (III) is carried out in the presence of formamidine acetate and trifluoroacetic acid in acetonitrile at the reflux temperature of the solvent and the subsequent treating with concentrated hydrochloric acid is carried out in ethyl acetate as solvent, at room temperature or slightly lower temperature.

* * * * *